United States Patent
Bar et al.

(10) Patent No.: US 11,701,099 B2
(45) Date of Patent: Jul. 18, 2023

(54) BALLOON DILATOR

(71) Applicant: MAZOR ROBOTICS LTD., Caesarea (IL)

(72) Inventors: Yossef Bar, Haifa (IL); Moshe Shoham, Hoshaya (IL)

(73) Assignee: MAZOR ROBOTICS LTD., Caesarea (IL)

( * ) Notice: Subject to any disclaimer, the term of this patent is extended or adjusted under 35 U.S.C. 154(b) by 0 days.

(21) Appl. No.: 16/301,443

(22) PCT Filed: May 15, 2017

(86) PCT No.: PCT/IL2017/050539
§ 371 (c)(1),
(2) Date: Nov. 14, 2018

(87) PCT Pub. No.: WO2017/199242
PCT Pub. Date: Nov. 23, 2017

(65) Prior Publication Data
US 2019/0290254 A1    Sep. 26, 2019

Related U.S. Application Data

(60) Provisional application No. 62/336,673, filed on May 15, 2016.

(51) Int. Cl.
*A61B 17/02* (2006.01)
*A61M 29/02* (2006.01)
(Continued)

(52) U.S. Cl.
CPC .......... *A61B 17/0218* (2013.01); *A61B 17/02* (2013.01); *A61M 29/00* (2013.01);
(Continued)

(58) Field of Classification Search
CPC .............. A61B 17/0218; A61B 17/02; A61B 2017/0225; A61M 29/00; A61M 29/02;
(Continued)

(56) References Cited

U.S. PATENT DOCUMENTS

| 3,868,956 | A | * | 3/1975 | Alfidi | A61B 17/22 606/194 |
| 5,282,847 | A | * | 2/1994 | Trescony | A61F 2/06 623/1.29 |

(Continued)

FOREIGN PATENT DOCUMENTS

WO    2015/040623    9/2014

OTHER PUBLICATIONS

PCT International Search Report and Written Opinion of the ISA, dated Aug. 10, 2017, in PCT/IL2017/050539 (already uploaded by USPTO on Nov. 14, 2018).

(Continued)

*Primary Examiner* — Ellen C Hammond
(74) *Attorney, Agent, or Firm* — Sheridan Ross P.C.

(57) ABSTRACT

A balloon dilator device, comprising an annularly shaped, cylindrical type structure having walls that are expandable from a radially collapsed state to a radially expanded state by inflation of a balloon inserted within the annular structure. Once the walls have been expanded, they remain in the expanded state even if the balloon is deflated, because the radially expanded state is a state of minimum mechanical potential energy, and in order to return to the collapsed state, the structure would have to pass a state of higher potential energy. The device walls require sufficient stiffness in their longitudinal direction to enable the device to be pushed into a minimally invasive incision made in the subject. This device stiffness can be achieved either by its mechanical material properties, or by its substantially closed wall struc- (Continued)

ture, or by use of a stiff protector sheath used to protect the walls during insertion.

17 Claims, 4 Drawing Sheets

(51) Int. Cl.
*A61M 29/00* (2006.01)
*A61B 17/00* (2006.01)

(52) U.S. Cl.
CPC ... *A61M 29/02* (2013.01); *A61B 2017/00557* (2013.01); *A61B 2017/00831* (2013.01); *A61B 2017/0225* (2013.01)

(58) Field of Classification Search
CPC .. A61F 2/4611; A61F 2002/4619; A61F 2/82; A61F 2230/005
See application file for complete search history.

(56) References Cited

U.S. PATENT DOCUMENTS

| | | | | |
|---|---|---|---|---|
| 5,476,506 A | * | 12/1995 | Lunn | A61F 2/06 623/1.13 |
| 5,571,173 A | * | 11/1996 | Parodi | A61F 2/07 623/1.13 |
| 5,578,072 A | * | 11/1996 | Barone | A61F 2/07 623/1.13 |
| 5,628,069 A | | 5/1997 | Ebert | |
| 6,277,136 B1 | * | 8/2001 | Bonutti | A61B 17/0218 600/204 |
| 6,893,460 B2 | * | 5/2005 | Spenser | A61F 2/2436 623/2.14 |
| 8,105,236 B2 | * | 1/2012 | Malandain | A61B 17/02 600/219 |
| 8,252,052 B2 | * | 8/2012 | Salahieh | A61F 2/2418 623/2.18 |
| 2001/0047198 A1 | * | 11/2001 | Drasler | A61F 2/07 623/1.13 |
| 2006/0004439 A1 | * | 1/2006 | Spenser | A61F 2/2433 623/1.23 |
| 2006/0147612 A1 | * | 7/2006 | Da Rocha Loures | A61L 31/10 427/2.25 |
| 2007/0010716 A1 | * | 1/2007 | Malandain | A61B 17/3403 600/224 |
| 2007/0112422 A1 | * | 5/2007 | Dehdashtian | A61F 2/2427 623/2.11 |
| 2008/0200943 A1 | | 8/2008 | Barker et al. | |
| 2011/0172697 A1 | * | 7/2011 | Jonsson | A61B 17/12036 606/194 |
| 2014/0039434 A1 | | 2/2014 | Kick et al. | |
| 2015/0127093 A1 | * | 5/2015 | Hosmer | A61F 2/2427 623/2.11 |
| 2017/0072173 A1 | * | 3/2017 | Van Dam | A61M 27/002 |
| 2019/0134358 A1 | * | 5/2019 | Jonsson | A61M 25/104 |

OTHER PUBLICATIONS

"Assembly Mode Changing in Parallel Mechanisms" published in IEEE Trans. Robotics, vol. 24, No. 4, pp. 765-772 (Aug. 2008).

\* cited by examiner

BALLOON DILATOR

FIELD OF THE INVENTION

The present invention relates to the field of dilators for surgical incisions, especially using single step methods of increasing the size of the incision to that required for the surgical procedure.

BACKGROUND OF THE INVENTION

Sets of dilators are used in surgery in order to create an opening into a patient's body in order to gain access for such tasks as surgical or endoscopic procedures. They are particularly useful for minimally invasive surgical procedures, since the opening need be no larger than is required for the desired access. Dilator sets currently in use comprises a series of dilator tubes of increasing diameter, each having a sharpened chamfered end so that they can be inserted with minimal tissue trauma, with the smallest diameter dilator tube inserted first, and the dilator tubes of increasing diameter inserted sequentially thereafter in order to enlarge the opening generated. Once the final and largest dilator tube has been inserted, the smaller inner ones can be removed, leaving a clear aperture for performing the desired surgical or endoscopic procedure. A mechanical dilator having an automatic insertion process activated by rotational mechanisms which can be power and/or robotically driven, is described in the PCT Application published as International Patent Application Publication No. WO/2015/040623 for "Automatic Dilator", having common inventors with the current application. Earlier prior art mechanical dilators are also described therein.

However, all such prior art dilator sets require considerable time in order to insert the successive dilator tubes one after the other, and the automatic dilator is mechanically complex.

There therefore exists a need for an automatic expansion dilator set which overcomes at least some of the disadvantages of prior art mechanical dilator sets.

The disclosures of each of the publications mentioned in this section and in other sections of the specification, are hereby incorporated by reference, each in its entirety.

SUMMARY

The present disclosure describes new exemplary automatic balloon dilator devices for generating minimally invasive access apertures for performing surgical procedures or endoscopic surveillance and operations. The devices use pneumatic inflation to enlarge the incision aperture, rather than the mechanical insertion of spreader tubes as in the systems of prior art dilator sets. The dilator devices of this disclosure utilize annular shaped mechanical structures having thin expandable or deployable walls, and an inflation balloon inserted down the axis of the annular shaped structure, and along the axial length that it is desired to expand. The unexpanded structure has a diameter sufficiently small that it can be inserted with minimal trauma in the position where the surgeon wishes to generate the incision aperture. Once the unexpanded structure has been inserted in place through the soft tissue, the axial balloon can be inflated, thereby causing the thin expandable or deployable walls of the structure to move radially outwards, and to radially distract the soft tissues surrounding the structure. The expansion process can be controlled and may be performed step-wise, and at a speed which does not cause excessive rupture of blood vessels or tearing of tissue in the region, thereby maintaining minimal trauma to the surrounding tissue. On the other hand, the process can be performed considerably more quickly than prior art devices, even automatically actuated ones using successive insertion of radially stacked tubes. It is also believed that the use of radially increasing pressure distraction of the tissue surrounding the incision generates less trauma than successive insertion of multiple spreader tubes, even when such tubes are chamfered to a sharp leading inside edge. The entire process can be robotically controlled, from the location of the dilator exactly over the region of interest within the bodily cavity, to the insertion process, which may be performed down a robotically held and directed guide tube, and including the inflation process of the axial balloon. The balloon may be inflated either by a gas such as compressed air, or by a liquid such as water driven by a compressor pump.

In order to provide a clear access aperture once the structure has been expanded to its finally desired diameter, the inflation balloon had to be withdrawn, and a mechanism is required in order to maintain the structure in its expanded form when the inflation balloon is withdrawn. Such structures can comprise a number of different mechanical forms. One form is a cylinder having walls which are collapsed into a corrugated form when the cylinder is in the insertion position, and when expanded to a larger circumferential dimension by inflation of the internal axial balloon, expands out to a second equilibrium position with the corrugations opened out, forming a cylinder with almost smooth walls.

If appropriately constructed, such a cylindrical wall has what is known as two-state mechanical stability, with each state being a state of mechanical equilibrium, and hence stable against limited mechanical compression attempting to change its shape. This bi-stable property enables the expanded cylindrical wall to maintain its expanded position, thus enabling the inflation balloon to be withdrawn without the cylinder collapsing.

Such bi-stable structures have been long-since known in bi-stable spring mechanisms for use, for instance, in such simple devices as electrical switches, bi-metal switches; and more recently, in threshold MEMS accelerometers, and the like. Such bi-stable structures have been illustrated in structures, such as, for instance in U.S. Pat. No. 5,628,069 for "Glove with Bistable Spring Element".

In such dynamical systems, there exist two stable equilibrium states, and the structure can be in a stable rest state in either of two states. In terms of potential energy, the structure has two local minima of potential energy separated by a local maximum, which is not an equilibrium position. The application of an external force—the inflating balloon in the present case—can switch the structure between its two bi-stable states. This implies that once the structure has switched to its stable expanded state, it will resist forces applied to return it to its collapsed state until those forces are sufficiently high as to enable the system to overcome the potential energy maximum between the two states, in order to return to its other stable state. This property is important for the operation of some of the inflatable dilators of the present disclosure, because it is the property which ensures that after deflation and extraction of the inflation balloon, the structure is able to withstand the inwardly directed forces exerted by the detracted tissues around the dilator, tending to force the dilator to collapse back to its undeployed state. The successful operation of the dilator is dependent on the ability of the structure to have a sufficiently high potential energy maximum in order to overcome the internal forces exerted by the surrounding tissue.

Another form of dilator structure can be a cylinder having a polygon form when deployed, whose side walls can be provided with longitudinal lines having weaker properties than the areas of the walls themselves, such as creases formed in the material during manufacture. The polygon walls may be folded inwards against each other in the undeployed state, forming a narrow internal bore into which the balloon is inserted and when the balloon is inflated, the creases open up causing the walls to swing out and form the deployed polygon shape. Such a structure may incorporate a locking latch on each pair of adjacent polygon sides, which lock the polygon when it reaches its expanded form. However, a structure involving a bi-stable equilibrium condition may be preferable since no additional latching mechanism is then required. In mechanical kinetic theory, these types of two state systems are known as "assembly modes" and have discrete solutions in the form of mechanisms that can remain in stable equilibrium in several configurations. Such examples and their theoretical development can be found for example in the paper titled "Assembly Mode Changing in Parallel Mechanisms" published in IEEE Trans. Robotics, Vol. 24, No. 4, pp. 765-772 (August 2008), having one of the inventors of the present application as a co-author.

An additional form of expandable dilator structure can be a smooth walled annular form, having its walls rolled up with layers of the wall overlapping each other, into a cylindrical form of small diameter, suitable for insertion into the initial incision made in the subject's skin. Once inserted, inflation of a balloon threaded down the axis of the initial coiled cylinder will cause the internal diameter to expand, such that the coiled walls unwind from each other, with the outer coil or coils of wall sliding over the inner ones as the coil unwinds. The inner and the outer edges of the thin sheet are equipped with a latching mechanism, such that as soon as the outer edge has completely unwound from the inner coils, the outer and inner edges lock together, forming a single cylinder of larger diameter and being locked in place by the latching mechanisms. This implementation has the disadvantage over the previously described expanding cylindrical or annular forms, in that part of the outer wall may have to slide circumferentially over the surrounding tissue as the device expands, but if the wall is sufficiently smooth, the friction will not impede the expansion, nor cause any significant additional trauma to the subject, since the unwinding of the coils should take place mostly from the inside of the coiled sheet. In this respect it is important that the inner surface of the coiled sheet be smooth so that the friction between the sliding coils of the sheets is reduced as much as possible.

The smoothness of the walls is important in order to provide a good seal around the dilator, so that blood does not enter the bodily cavity, and so that tissue does not get trapped within any slots down the length of the expanded cylinder.

The outer annular walls of the mechanical structure can take any cylindrical or annular mechanical form, provided that some form of locking mechanism is provided to keep the form from collapsing when the inflation balloon is deflated and withdrawn. A common feature of the implementations of the presently disclosed devices is that the overall full length of the circumferential annular walls when fully extended, are fitted into a smaller diameter device when unextended, by means of some form of folding or ridging or overlapping sections. The walls can be made of any material which provides the appropriate folding or creasing properties, whether metallic or polymeric.

Since these dilators are constructed of mechanically connected walls, and may have comparatively sharp circumferential features, and more probably, comparatively sharp leading edge features, it is important that the subject's tissues be protected from damage which may be caused by such sharp protrusions or features during insertion of the collapsed dilator. Consequently a protective sheath may often be required for the dilator, into which the expandable structure is fitted during the insertion process into the initial puncture aperture. If the sheath is made of a flexible polymer material, it can remain within the aperture while the expansion process is being performed. If it is a stiff sheath, then it should be withdrawn before inflation of the balloon commences, or it should have longitudinal sections that can detach from each other so as not to impede the inflation of the balloon. If the outer wall features of the structure are comparatively smooth, it may be sufficient to provide only an end cap, which fits over the distal end of the dilator structure, to prevent injury by any sharp points or corners on the front end of the structure, or a protecting device may not=be necessary at all.

The above-mentioned structures all utilize folding or unbending mechanical parts in order to increase diameter of the structure. Other implementations can be provided in which the structure has flexible polymer walls, which thus readily expand when the inflation balloon is inflated within them, but which are adapted to harden after they reached the desired fully extended size. A simple method of achieving this is by the use of epoxy compounds, which can be hardened catalytically or by exposure to ultraviolet light. The compounds can most simply be contained between the walls of a double-walled annular elastomer jacket, and the catalytic hardener activated by the applied pressure of the inflation balloon, or by the insertion of an ultraviolet light source, such as a UV emitting diode, alongside or within the inflating balloon.

The walls of the dilators described in this disclosure may be advantageously implemented as closed or continuous or unbroken sheets, in the sense that there is no need for any openings or holes or spaces in the walls. In this respect the devices of the present disclosure are generally distinct from structures such as stents, which are also devices which are expanded from a smaller size to a larger size by means of balloon inflation, but which generally are constructed of open mesh or trellis walls. Since the dilator devices of the present disclosure must be able to exert substantial outward directed radial pressures in order to compress the surrounding tissues, they cannot have a large fraction of their wall areas open, since the tissues in which the dilator is being deployed would then bulge through these openings into the dilator bore, causing a more limited central aperture and possibly trauma to the tissue. Therefore while it is not imperative that the walls of the dilators of the present disclosure be completely closed or continuous or unbroken, any openings therein should be limited to a minor part of the total area of the walls. While not applying any strict criteria to this feature, dilator walls having more than 50% of their area open, are not expected to be effective for the dilator functions expected. On the other hand, openings of the order of 25% of the wall area, would appear to enable the functioning of an efficient dilator, though this level is not intended to be a strict criterion. Walls which fulfil these requirements are described in this disclosure, and are likewise claimed, as "substantially closed walls". Therefore, although the various specific implementations of the dilator devices of the present disclosure are shown and described using solid, continuous walls, it is to be understood that this is not a strict requirement, but that any open regions in the walls could be limited to a minor part of the wall area.

A further differentiation from stents for use in blood vessels or other bodily lumens, arises because such stents generally have mesh walls because of the need to maneuver the device through the blood vessels or other bodily lumens to the position at which they are to be located. This property of flexibility, on the other hand, is unsuitable for use in the walls of the dilators described in this disclosure, since the device must have sufficient stiffness along its axial length (longitudinally) so that it can be pushed into an incision made in the soft tissues of a subject. This action possibly requires significant applied forces, since the incision is generally made as small as possible to minimize trauma. A mesh walled device of the type used in stents would thus be unsuitable for this use, as it may not withstand the applied longitudinal forces necessary. Therefore, the dilators described in this disclosure need to have walls having substantial stiffness in their longitudinal direction, such that they can be inserted into a minimally invasive incision made in the tissues of a patient. The level of "substantial stiffness" is dependent on such factors as the type of tissue at the incision site, the thickness of the tissue wall through which the dilation device has to penetrate, and the lateral size of the incision, all of which are dependent on the particular procedure to be carried out, and on the patient's anatomy. As an alternative, if the dilator is to be used with a protective sheath, as previously mentioned, and the protective sheath is sufficiently stiff in its longitudinal direction, then the need for stiffness along the length of the walls of the dilator structure may be relaxed.

The cylindrical or annular structure can be fitted with suction and irrigation tubes attached integrally to the inside of the expanding walls, and can also have an optical fiber for providing illumination within the bodily cavity into which the dilator device is to be inserted.

After the surgical procedure, the expanded cylindrical structure can be simply withdrawn by pulling out of the expanded incision aperture.

There is thus provided in accordance with an exemplary implementation of the devices described in this disclosure, a balloon dilator device, comprising a longitudinally elongated, annularly shaped structure, the structure being expandable from a radially collapsed state to a radially expanded state by inflation of a balloon inserted within the structure, wherein the structure has a mechanical stiffness in its longitudinal direction sufficient that the device can be pushed into an incision made in a subject, and wherein the radially expanded state is a state of minimum mechanical potential energy, such that the structure maintains its expanded state when the balloon is deflated.

In such a device, the mechanical stiffness may be provided by virtue of the mechanical stiffness of the material and the shape of the structure, or by virtue of the structure having substantially closed surfaces. In the latter case, the substantially closed surfaces may have no more than 50% of their surface as openings, or in a further implementation, no more than 25% of their surface as openings.

Additional implementations of such devices may further comprise an annular sheath having inner dimensions such that the device in its radially collapsed state fits within the annular sheath, the annular sheath being expandable with expansion of the annularly shaped structure. In such an implementation, the mechanical stiffness of the device in its longitudinal direction may be provided by virtue of the annular sheath in its unexpanded form.

In any of the above-described implementations of the balloon dilator device, the structure may be formed with at least one of corrugations, folds or creases directed along its length. Alternatively, the structure may comprise a section of loosely coiled sheet, in which at least a first part of the coiled sheet overlaps a second part of the coiled sheet.

Additionally, alternative implementations of any of the above-described systems may further involve a balloon dilator device comprising an annularly shaped structure disposed in a radially collapsed state, the structure having an initial outer diameter, and an inner diameter adapted to receive an inflation balloon, such that when the balloon is inflated, the walls deploy radially from their collapsed state, such that the initial outer diameter expands to a final outer diameter which is maintained after deflation of the balloon, wherein the annularly shaped structure has mechanical properties providing bistable mechanical states, and the final outer diameter is maintained by means of one of the bistable mechanical states.

Alternatively, in such a balloon dilator device, the final outer diameter may be maintained by means of a mechanical latching device, or by means of a hardenable compound activated to harden the structure after inflation of the balloon.

In further implementations of such a balloon dilator device, the annularly shaped structure may comprise a double-walled annular pouch, comprising a first and a second sheet of flexible material, and a hardenable flexible compound disposed between the first and second sheets. The hardenable compound may be an epoxide compound, hardened by a chemical catalytic substance. In that case, the chemical catalytic substance may be contained within capsules dispersed within the flexible compound, the capsules having outer walls which have a rupture strength predetermined such that the outer walls rupture under the pressure generated by inflation of the inflation balloon. Alternatively, the hardenable compound may be a photochemical compound cured by exposure to ultra violet light.

Yet another implementation of such balloon dilators may comprise an expandable annular walled structure having:

(i) a first equilibrium state, in which the walls are formed such that the structure has an internal dimension and a first external dimension, and (ii) a second equilibrium state, in which the walls have a second external dimension, larger than the first external dimension, wherein the transition from the first equilibrium state to the second equilibrium state is achieved by means of an inflatable balloon adapted to be disposed within the walls, and wherein the second equilibrium state is achieved by passing through a state of greater mechanical potential energy than that of the second equilibrium state, such that the second external dimension is maintained even when the inflatable balloon is deflated.

Finally, still other example implementations involve a method of dilating an incision through the soft tissue of a subject, the method comprising:

(i) making an incision in a soft tissue of a subject, the incision being sufficiently large to enable insertion of a balloon dilator device, and being expandable from a radially collapsed state to a radially expanded state, (ii) inserting the balloon dilator device into the incision, (iii) inflating a balloon disposed within the radially collapsed state of the balloon dilator device, such that the balloon dilator device expands to the predetermined radially expanded state, and (iv) withdrawing the inflation balloon, such that access through the soft tissue of the subject is enabled through the expanded balloon dilator device.

It is to be noted that in this disclosure, the term annular is used in its broad sense of a ring-like shape, whether the ring is geometrically circular or not. Likewise, the term cylindrical is not intended to be limited to the conventional mathematical use of the word cylindrical, meaning the surface formed by points at a fixed distance from a given straight line, or a right circular cylinder, but is intended to cover any structure which has a generally parallel walled, tube-like structure, whether the annular walls are arranged circularly and smooth, as is understood by the conventional mathematical use of the word cylindrical, or oval-shaped, or whether the walls do not have a pure circular or even oval shape, but may be made up of separate circumferential annular wall segments, so long as those segments form a completely closed outer wall of the so-called cylinder.

BRIEF DESCRIPTION OF THE DRAWINGS

The present invention will be understood and appreciated more fully from the following detailed description, taken in conjunction with the drawings in which.

DETAILED DESCRIPTION

Figure 1A:
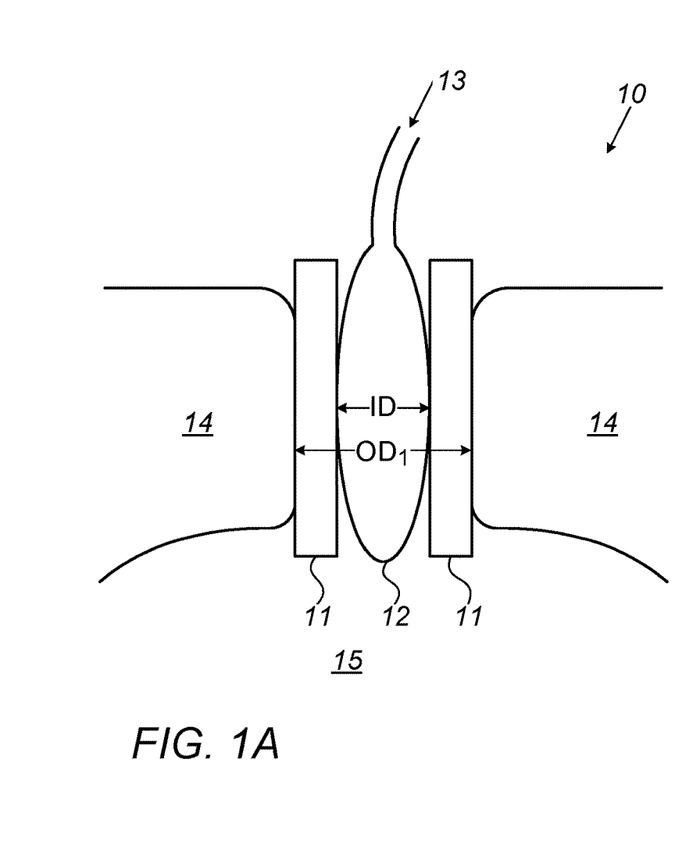
FIGS. 1A and 1B illustrate schematically an automatic balloon dilator of the present disclosure, in its stowed and deployed situations respectively.
Figure 1B:
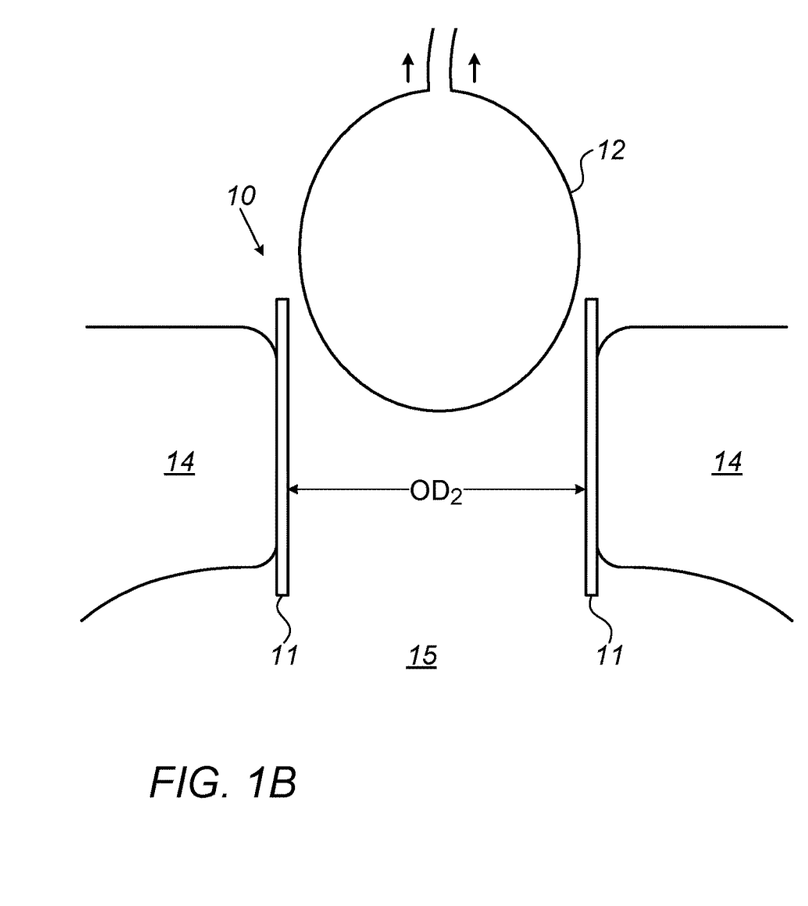

Reference is now made to FIGS. 1A and 1B, which illustrate schematically an automatic balloon dilator of the present disclosure, and the difference in its structure before and after deployment. The dilator 10 has external annular walls 11, having an inner dimension ID and an outer dimension $OD_1$. The axially directed cross-section of the annular structure can be either circular, or oval, or polygonal, or any other suitable shape. In its undeployed state, the dilator has an outer dimension which enables it to be inserted in a minimally invasive puncture in the soft tissue 14 of the subject, as shown in FIG. 1A, such that the distal end of the dilator enters the body cavity 15 to which the dilator is intended to provide access. A robotic arm with a guide tube and tubular applicator (not shown in FIGS. 1A and 1B) may be used in order to ensure accurate positioning and placement of the dilator. An inflation balloon 12 located in the bore of the dilator, is slowly expanded by means of externally applied pressure 13, which can be by means of gas or liquid pressure. As the balloon expands radially, it forces the specially shaped form of the walls 11 to unfold or deploy, which results in an outward radial motion of the external annular walls 11, thereby expanding the soft tissue 14 such that the aperture in the tissue 14 becomes enlarged. The wall structure is designed such that when it is completely deployed or unfolded, the outer dimension of the walls have stretched the tissue 14 such that the aperture in the soft tissue has reached the desired size, $OD_2$, and the balloon expansion can be ceased. The deployed or unfolded shape of the external walls is indicated in FIG. 1B by the much thinner dimension of the wall itself 11, the difference in wall thickness between FIG. 1A and FIG. 1B being attributed to the unfolding or deployment of the initial structure of the external annular walls. The walls are maintained in their expanded form by means of a mechanism which prevents them from collapsing again. At this point the inflation balloon 12 can be deflated and removed, as shown in FIG. 1B, thereby providing clear access of diameter $OD_2$ to the bodily cavity for any intended surgical or endoscopic procedure.

Figure 1C:
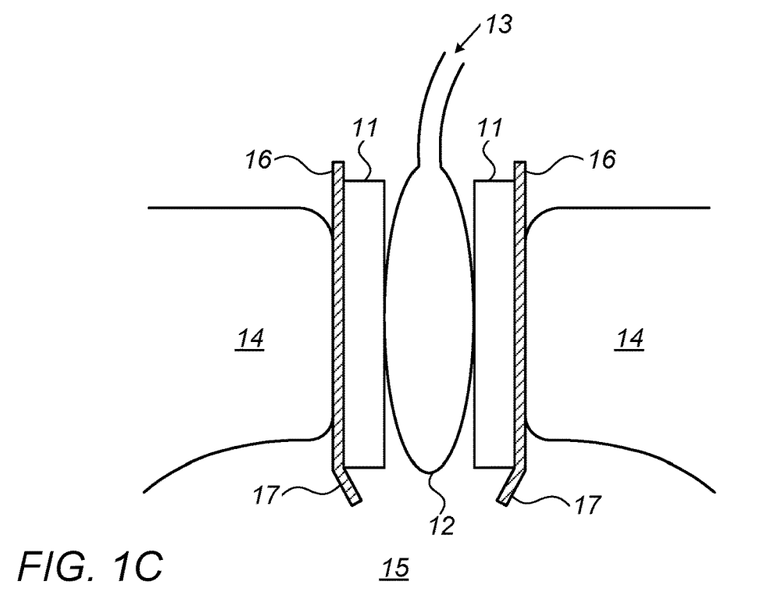
FIG. 1C shows the dilator of FIGS. 1A and 1B including an insertion sheath.

Reference is now made to FIG. 1C, which illustrates a generic balloon dilator as illustrated in FIG. 1A, with an exemplary protective sheath surrounding it, such that it can be inserted into the initial puncture aperture without causing unnecessary damage to the soft tissues into which the device is being inserted. In FIG. 1C, all of the component parts have the same numbering as in FIGS. 1A and 1B. The exemplary sheath 16 of FIG. 1C is shown as a smooth cylindrical tube surrounding the outer wall of the folded dilator structure, such that any sharp edges on the outer wall of the folded structure 11 is prevented from coming into contact with the tissues 14 at the inner edge of the aperture. In addition, this example of the sheath has an optional front shield 17, which covers the front end of the device, to reduce any tissue damage that may be caused by the front edges during insertion, and also having a cone-shaped profile to ease insertion. Use of such a sheath also provides strength to the undeployed structure, which may be so fragile in that undeployed state that insertion without a sheath could cause it to crumple under the forces of the insertion. The sheath may be constructed of a stretchable polymeric material, such that it may be left in place during the balloon inflation, or it may be constructed of an unstretchable material such as a metal, for use only during insertion of the dilator into the subject's tissues, and for withdrawal before balloon inflation. In the latter case, it may not be possible to incorporate a front shield 17, since that would interfere with withdrawal of the sheath. Alternatively, it could be constructed of two or more longitudinal segments, attached to each other by a weak bond, such as, for instance, a thinner membrane region or a weak adhesive. The sheath may thus initially be inserted as once complete element to protect the folded dilator structure during insertion, but will split lengthwise into separate segments when the balloon begins the dilation process, so that it does not impede the dilation.

A number of different mechanisms are available for providing the features which maintain the deployed annular external walls in their expanded situation. Some of these methods utilize a structure having two state stability, both in the undeployed uninflated situation shown in FIG. 1A, and in the fully deployed situation, shown in FIG. 1B.

Figure 2:
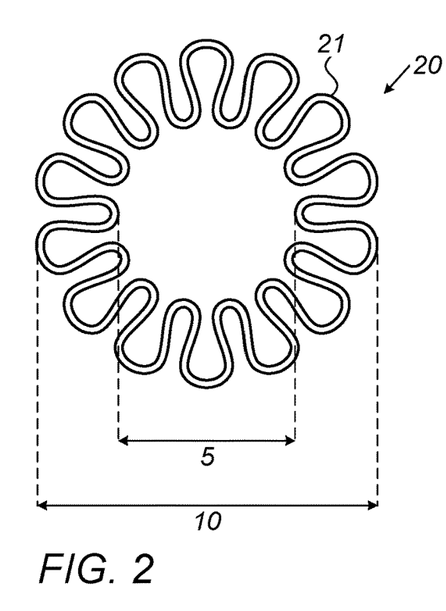
FIG. 2 is a cross-sectional schematic view of the mechanical annular wall structure of an automatic balloon dilator of the type shown in FIGS. 1A and 1B, using a folded external wall configuration.
Figure 3:
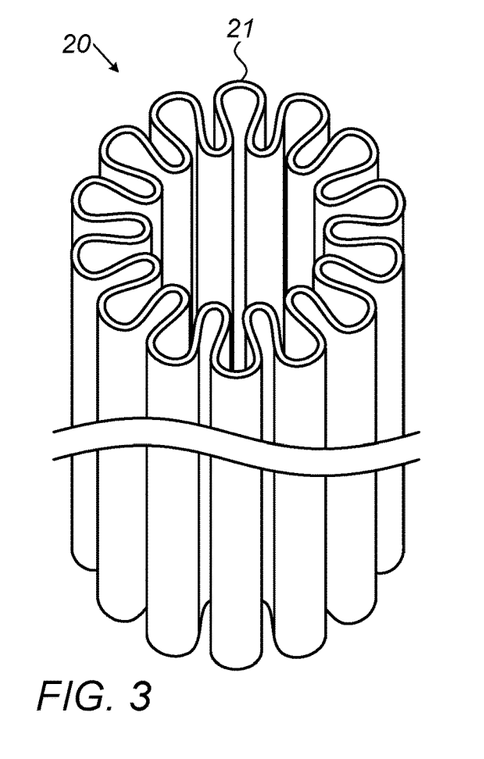
FIG. 3 is an isometric schematic view of the mechanical annular wall structure of the automatic balloon dilator of FIG. 2.

Reference is now made to FIGS. 2 and 3, which illustrate schematically one such structure having mechanical equilibrium both in the collapsed state and in the deployed expanded state. In the collapsed state, the exemplary device has an internal diameter of 5 mm, and an external diameter of 10 mm. FIG. 2 is a cross-sectional view of the annular walls of the structure 20, looking axially down the dilator. The walls of the structure have been formed as corrugated folds 21, either during manufacture of the device, or by folding or creasing a smooth walled device after manufacture. The total length of the folded corrugations 21, if stretched out, would represent a circumferential length of an annular device having a substantially larger outer diameter than that of the corrugated folded device. Thus, the folded corrugations enable the generation of a device having substantially smaller inner and outer dimensions than the total length of the walls would represent as a circular cylinder, if they were to be "straightened out". As the internal balloon inflates, it forces the folds of the corrugations to straighten out, and the total circumferential length of the straightened out folds is indicative of a device having a much larger diameter than when the folds are still undeployed. In the expanded condition, the mechanical properties of the walls are such that the expanded form is maintained under equilibrium without a tendency to collapse back into the folded form. FIG. 3 is an isometric schematic view of such an annular expandable dilator device, showing the folded corrugations down the length of the device, and the length of the device for passage through the soft tissue into the patient's bodily cavity.

Figure 4:
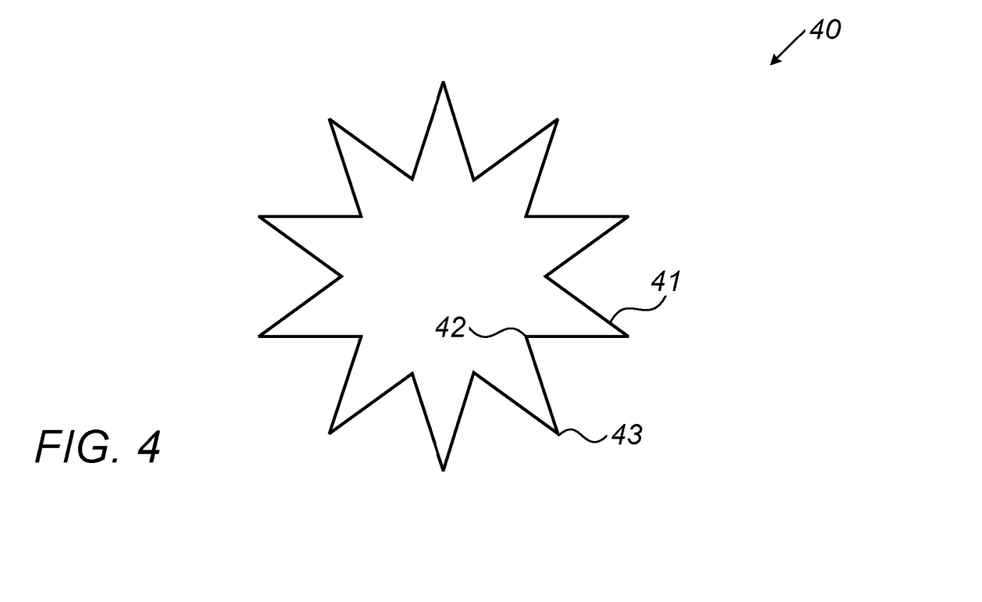
FIG. 4 is an alternative structure to that shown in FIGS. 2 and 3, and in which the walls of the annular structure are made of sheet folded such that they form a sharply angled, folded, star-shaped structure.

Reference is now made to FIG. 4 which is a cross sectional view of an alternative structure 40 to that shown in FIGS. 2 and 3, and in which the walls 41 of the annular structure are made of sheet folded such that they form a sharply angled, folded, star shaped structure, having, like the implementations of FIGS. 2 and 3, a substantially smaller diameter than would be obtained if the sheets were unfolded. The folds can be formed by means of longitudinal creases 42, 43, parallel to the axis of the dilator device. When the device is fully deployed by inflation of the axially located balloon (not shown), the folds open out to form a polygon-shaped annular structure, close to a circular form. The optimum way of keeping that shape deployed is by designing the structure to be mechanically bistable, namely, having two equilibrium states, though a mechanical latching method may also be used but is generally more complex to manufacture and to enable reliable operation.

Figure 5A:
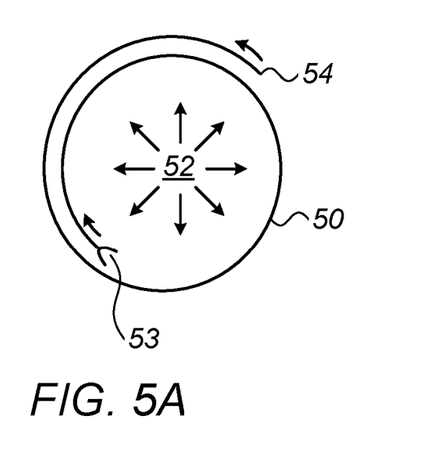
FIG. 5A shows schematically a cross-sectional view of an alternative implementation of the devices of the present disclosure, in which the annular walls are in the form of a coiled sheet.

Reference is now made to FIG. 5A, which shows a cross-sectional view of an alternative implementation of the devices of the present disclosure, in which the annular walls are in the form of a coil of sheet 50, in which a section of one end of the coiled sheet overlaps the sheet at a second end, and which uncoils as internal outward radial pressure 52 is applied by activation of the inflation balloon (not shown), and therefore expands the diameter of the annular walled structure. The possible motion directions of the ends of the coiled sheet are shown in FIG. 5A by the arrows next to these extremities. In order to ensure that the outward pressure of the inflation balloon causes the coil to unwind, rather than just forcing and locking the coiled layers against the tissue of the insertion puncture, it is important that the friction between the layers of the sheets and between the outer face of the sheets and the tissue be reduced to as low a value as possible. For the overlapping layer between the sheets, this could be achieved by an anti-friction layer or by a bio-compatibly acceptable lubricant. Additionally, the use of more than approximately one addition half-circumference of overlap may exacerbate the above-mentioned problem, and make the unwinding process problematic. It is possible to arrange the inflation balloon characteristics, such as by use of longitudinal stiffeners that will limit the expansion in some radial direction, and by arranging the orientation of the balloon so that the outward expansion is applied preferentially along a direction parallel to an axis connecting the initially free ends, 53, 54, of the coiled sheet, thereby forcing those ends apart while reducing the application of pressure in other radial direction that would tend to force the coiled sheet layers together and impede their unwinding.

Figure 5B:
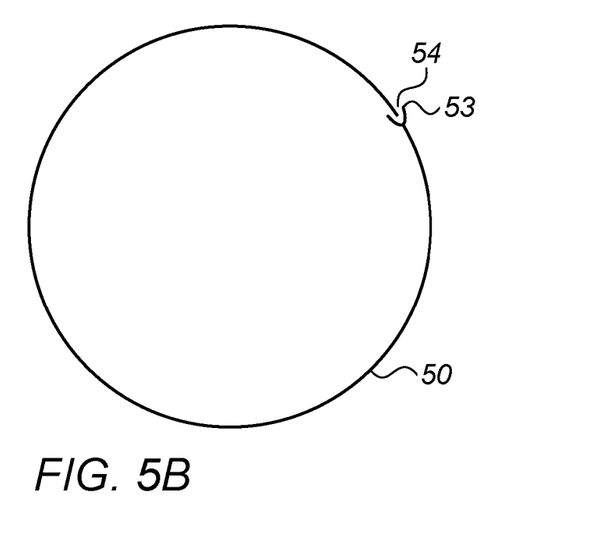
FIG. 5B shows the device of FIG. 5A after full expansion has been achieved and the walls have latched into the locked position. in a deployed situation.

The innermost and the outermost edges of the thin sheet are equipped with a latching mechanism, such that as soon as the outer edge has completely unwound from the inner coils, the outer and inner edges lock together, forming a single cylinder of larger diameter and being locked in place by the latching mechanism. In the implementation shown in FIG. 5B, which shows the device of FIG. 5A after full expansion has been achieved and after the walls have latched into the locked position. in a deployed situation. In this example, the mechanical latching is achieved in an exemplary manner by having a trough shaped edge 53 to the inner end of the coiled sheet, into which the sharp outer edge 54 slips the moment the coil is fully opened. The natural tendency of the sheet to recoil itself may be used to hold the outer edge 54 firmly into the trough shaped inner edge 53 of the sheet. However it is to be understood that this is only one example of how the structure may be latched open, and is not intended to limit the inventive scope of the devices shown.

Figure 6:
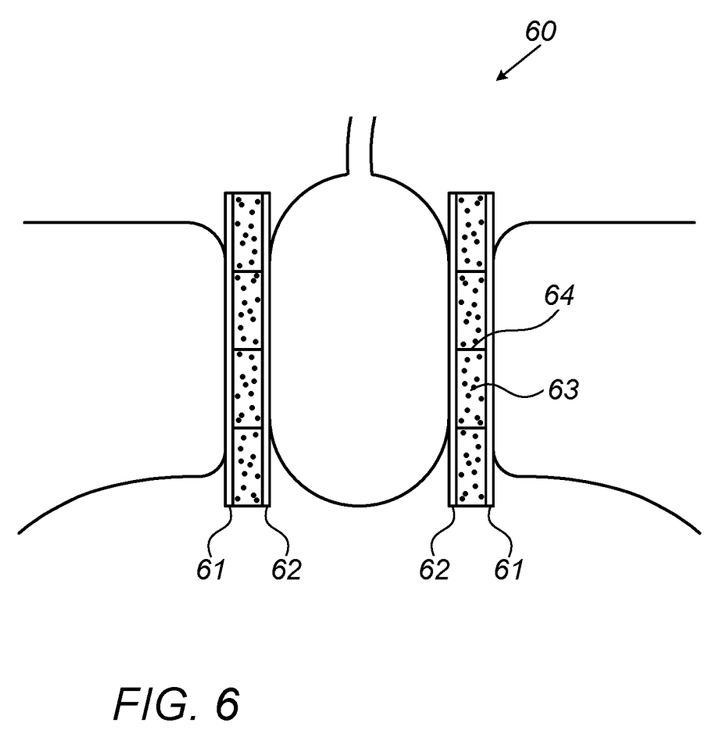
FIG. 6 illustrates schematically a double skin structure with a compound between the skins which hardens under the pressure applied by the inflatable balloon.

Reference is now made to FIG. 6, which illustrates schematically a further implementation of a structure 60 for use in the dilators of the present disclosure. This structure utilizes the hardening properties of a chemical compound in order to maintain the fully opened diameter of the dilator, after the balloon has expanded the dilator structure to its desired size. According to one exemplary method of accomplishing this, the walls of the dilator are made of a double layer of polymer sheet 61, 62, in the form of an annular pouch, with a chemical compound 63 between the layers, which can be hardened by application of the correct conditions. The distance between the sheets can be made as small as the strength of the hardened layer allows, and the distance shown in FIG. 6 has been exaggerated in order to show the construction clearly. One convenient way in which this hardening can be achieved is by the use a resin compound, such as an epoxy composition, with small capsules of the curing compound dispersed therein. The capsules are shown in FIG. 6 as the small dots dispersed within the epoxy 63. The outer skins or walls of the capsules have a rupture strength predetermined to be at a level such that the pressure of the balloon inflation on the walls of the device causes the capsules to rupture, and the curing agent to mix with the epoxide compound, and thus to harden it. Epoxide systems are available that can cure to a solid within 30 seconds, such that the stiff, expanded shape of the dilator is readily obtained. Fabrication of such an implementation is simple and of low cost. Any alternative method of hardening the epoxy layer can also be used, such as the use of ultraviolet light on a light sensitive epoxy layer, which then undergoes photochemical polymerization and hardens. The UV light can be readily applied to the epoxy layer using a UV LED array, which can be conveniently be disposed inside the balloon. For such light cured configurations, the polymer sheets of the walls of the device should be transparent to the UV wavelength used.

If an annular double walled jacket having a single continuous cell is used for the expandable dilator structure, there is a possibility that as the balloon expands, it will exert the maximum pressure in the central part of the jacket, forcing the thick fluid or gel-like uncured epoxy away from the center of the jacket and towards the distal and proximal ends of the jacket. As a result, the thickness of the central region of the jacket will be substantially smaller than that at ends of the jacket, and there would then be danger that the central region would not have sufficient strength when cured to withstand the forces applied to them by the surrounding tissues, when the inflation balloon is removed and the walls cured. In order to avoid this effect, means must be taken to prevent the epoxy from migrating to the ends of the jacket. In order to maintain such a desired even concentration of the material over the whole length of the annular pouch, it can be divided into several separate compartments by means of circumferential dividers 64 along the length of the annular pouch. Alternatively, the whole of the area of the double walled jacket could be composed of separate cells, such as in a honeycomb pattern.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A dilator device for insertion into a minimally invasive incision aperture made in a tissue, the dilator device comprising:
    a longitudinally elongated structure having an annular wall that expands under application of an externally applied outwardly directed mechanical force from a radially collapsed state to a radially expanded state when the externally applied outwardly directed mechanical force is applied to the annular wall from within the structure, such that the annular wall of the structure enlarges the minimally invasive incision aperture,
    wherein the radially collapsed state and the radially expanded state are bistable mechanical equilibrium states having local minima of potential energy separated by a local maximum which is not an equilibrium position, the potential energy of the radially expanded bistable state being sufficiently less than the local maximum potential energy that, when the mechanical force is relaxed after insertion of the structure into a tissue of a subject, the annular wall remains in the radially expanded state, and
    wherein the structure in its collapsed state has, in a longitudinal direction, a mechanical stiffness that enables the device to be pushed into the minimally invasive incision aperture made in the tissue.

2. A dilator device according to claim 1, wherein the mechanical stiffness of the structure is provided by virtue of the mechanical stiffness of a material and a shape of the structure.

3. A dilator device according to claim 1, wherein the mechanical stiffness is provided by virtue of the structure having substantially closed surfaces.

4. A dilator device according to claim 3, wherein the substantially closed surfaces have no more than 50% of their surface as openings.

5. A dilator device according to claim 3, wherein the substantially closed surfaces have no more than 25% of their surface as openings.

6. A dilator device according to claim 1, further comprising an annular sheath having inner dimensions such that the device in its radially collapsed state fits within the annular sheath, the annular sheath being expandable with expansion of the annular wall.

7. A dilator device according to claim 6, wherein the annular sheath in its unexpanded form, is configured to provide the structure with the mechanical stiffness in its longitudinal direction.

8. A dilator device according to claim 1, wherein the annular wall is formed with at least one of corrugations, folds or creases directed along its length.

9. A dilator device according to claim 1, wherein the structure comprises a section of coiled sheet, wherein at least a first part of the coiled sheet overlaps a second part of the coiled sheet.

10. A dilator device according to claim 1 wherein the annular wall in its radially collapsed state has an initial outer diameter and an inner diameter adapted to receive the externally applied outwardly directed mechanical force, and wherein when the force is applied, the annular wall deploys radially from the radially collapsed state and the initial outer diameter expands to a final outer diameter which is maintained after relaxation of the force.

11. A dilator device according to claim 1 wherein the radially expanded state is maintained by means of a mechanical latching device.

12. A dilator device according to claim 1, wherein the externally applied outwardly directed mechanical force results from the inflation of a balloon inserted within the structure.

13. A dilator device according to claim 12, wherein the radially expanded state state is maintained even when the inflatable balloon is deflated, since the local maximum of potential energy between the radially collapsed state and the radially expanded state is sufficiently high that forces applied by the aperture in the subject into which the dilator is inserted, are not sufficiently high to overcome the state of higher local maximum potential energy to return the device to its radially collapsed state.

14. A dilator device for insertion into an initial puncture aperture in a soft tissue of a subject, the dilator device comprising:
    an expandable annular walled structure having two equilibrium states:
        a first equilibrium state having a first level of mechanical potential energy, in which the walled structure has a first dimension; and
        a second equilibrium state having a second level of mechanical potential energy, in which the walled structure has a second dimension, larger than the first dimension, the walled structure being adapted to undergo the transition from the first equilibrium state to the second equilibrium state by application of an externally applied, outwardly directed mechanical force from within the walled structure, such that the walled structure enlarges the initial puncture aperture in the soft tissue of the subject,
    wherein the second equilibrium state is achieved by passing through a transition state having a third level of mechanical potential energy, the third level being greater than each of the first level and the second level, such that the second external dimension is maintained even when the applied force is relaxed, and wherein the annular walled structure in its first equilibrium state has a stiffness along its axial length that enables the structure to be pushed into the initial puncture aperture in the soft tissue of a subject.

15. A dilator device according to claim 14, wherein the initial puncture aperture is a minimally invasive incision.

16. A dilator device according to claim 14, wherein the externally applied outwardly directed mechanical force results from the inflation of a balloon inserted within the walled structure.

17. A dilator device according to claim 16, wherein the second equilibrium state is maintained even when the inflatable balloon is deflated, since the state of greater mechanical potential energy between the second and the first equilibrium states is sufficiently high that forces applied by the aperture in the subject into which the dilator is inserted, are not sufficiently high to overcome the state of greater mechanical potential energy to return the device to its first equilibrium state.

\* \* \* \* \*